United States Patent
Sjölund et al.

(10) Patent No.: US 8,743,662 B2
(45) Date of Patent: Jun. 3, 2014

(54) REPLACEABLE CAP FOR A DOSING DEVICE

(71) Applicant: Patients Pending Ltd, London (GB)

(72) Inventors: Per John Sjölund, London (GB); Marcel Botha, Bellville (ZA); Per Andreas Sjölund, Stockholm (SE)

(73) Assignee: Patients Pending, Ltd, London (GB)

( * ) Notice: Subject to any disclaimer, the term of this patent is extended or adjusted under 35 U.S.C. 154(b) by 24 days.

(21) Appl. No.: 13/724,183

(22) Filed: Dec. 21, 2012

(65) Prior Publication Data

US 2014/0018733 A1     Jan. 16, 2014

Related U.S. Application Data

(63) Continuation of application No. PCT/IB2011/001517, filed on Jun. 29, 2011.

(30) Foreign Application Priority Data

Jul. 1, 2010   (NL) ...................................... 2005017

(51) Int. Cl.
    *G04B 47/00*     (2006.01)
(52) U.S. Cl.
    USPC .......................................................... 368/10
(58) Field of Classification Search
    USPC .............. 368/10, 12, 107, 113, 108, 118, 120
    See application file for complete search history.

(56) References Cited

U.S. PATENT DOCUMENTS

| | | | |
|---|---|---|---|
| 5,751,661 A * | 5/1998 | Walters | 368/10 |
| 6,707,763 B2 | 3/2004 | Osberg | |
| 6,845,064 B2 * | 1/2005 | Hildebrandt | 368/10 |
| 7,133,329 B2 | 11/2006 | Skyggebjerg | |
| 7,362,660 B2 * | 4/2008 | Hildebrandt | 368/10 |
| 7,907,477 B2 * | 3/2011 | Puzia | 368/10 |
| 2002/0096543 A1 | 7/2002 | Juselius | |
| 2002/0126585 A1 | 9/2002 | Osberg et al. | |
| 2004/0062148 A1 | 4/2004 | Skyggebjerg et al. | |

FOREIGN PATENT DOCUMENTS

| | | |
|---|---|---|
| WO | 99/43283 A1 | 9/1999 |
| WO | 03/063754 A1 | 8/2003 |

\* cited by examiner

*Primary Examiner* — Edwin A. Leon

(74) *Attorney, Agent, or Firm* — Danial A. Thomson; Emerson Thomson Bennett, LLC

(57) ABSTRACT

A replaceable cap (10) for a transdermal liquid dosing device (12) such as an insulin pen is provided. The cap includes an elongate hollow body (14) with a first open end (16) which can be placed over a front part (26) of the dosing device and a second closed end (18) opposite the first end. The cap body also includes a cavity which opens into the interior (50) of the cap body and which houses a control unit (52) which includes a timer unit, a switch mechanism (56) that stands at least partially proud of the cavity, so as to project into the interior of the body, and a timer display unit (58) which displays time counted by the timer unit on an outer surface of the body of the cap. The switch mechanism is engaged by abutment of a surface of the front part of the dosing device when the cap is placed on the dosing device, and released when the cap is removed from the dosing device, the engagement and/or releasing of the switch mechanism causing the timer unit to reset after the elapse of a predetermined period of time, the time since the timer unit was last reset thereby indicating the time that has elapsed since the dosing device was last used.

15 Claims, 4 Drawing Sheets

REPLACEABLE CAP FOR A DOSING DEVICE

FIELD OF THE INVENTION

This invention relates to a replaceable cap for a dosing device and more specifically to a replaceable cap for a transdermal liquid dosing device such as an insulin pen.

BACKGROUND TO THE INVENTION

Insulin dependent diabetics are required to adhere to a strict prescribed regimen of liquid insulin injections in order to manage their diabetes. One popular means of administering insulin is by means of a reusable transdermal liquid dosing device commonly referred to as an "insulin pen", which includes a plastic syringe with an insulin reservoir and a cap that covers a proximal end of the syringe from which the insulin is delivered by means of a hypodermic needle.

It is known from several published studies that because diabetics are required to take multiple daily injections of insulin, the injecting procedure very quickly becomes so routine that an individual dose can easily be forgotten. There is generally no simple and reliable way to tell—using commonly prescribed insulin pens or by examining the injection area—whether or not a given dose has been administered. Missing a prescribed insulin dose or inadvertently taking too many doses within a short period of time can lead to serious short and long-term health risks and complications for a diabetic person, including hyperglycaemia and hypoglycaemia.

Several attempts have been made in the past to solve this problem. For example, US-2009/0076458 to Nielsen describes an injection device that is itself capable of emitting a flashing light signal indicating the time elapsed since the last injection. The flashing light is provided on the body of the device. While US-2009/0076458 seeks to solve the same problem as the present invention, it has the disadvantage of forcing a diabetic person to abandon and discard their preferred or prescribed insulin delivery system in favour of a new system, which may be economically prohibitive for many users. Another disadvantage of the injection device disclosed in US-2009/0076458 is that the user would have to learn the meaning of the particular flashing light sequence used to indicate the time since the last injection. This could be a significant obstacle for some diabetics, in particular the young or elderly.

US-2004/0062148 to Skyggebjerg discloses a timer device that includes two device portions that detach from each other and together form a single portable unit. An insulin pen in provided in one of the device portions and the two device portions are held together when the pen is not in use. Separation of the device portions causes a control action to be actuated. This solution suffers from the disadvantage that the preferred embodiment is complex and requires a measure of user sophistication and discipline in using the device, as well as requiring a separate dedicated and larger device to be carried. In other described embodiments, one of the device portions is integral with a cap adapted to cover a distal portion of the first device. The disclosure is silent on any practical or cost-effective means of detecting separation of the device portions in that described embodiment or ensuring proper cooperation between the cap and distal portion of the first device.

Systems have been proposed in which medication devices are placed in register with docking-stations that function as control and indicating devices, for example WO-03/063754 and WO-99/43283, the latter of which discloses a sleeve-like indicating device that can be attached to the rear end of an injection pen. These devices suffer from the disadvantage that an additional piece of equipment must be used in conjunction with the insulin pen, and are generally complex and expensive.

US 2002/0096543 discloses a portable control device for monitoring doses of insulin administration. In certain disclosed embodiments, a control device is provided as a separate piece that can be fixed to a conventional cap of an injection pen, and the body of the pen includes a resonance circuit to enable removal of the cap to be detected. The control device includes a transmitter that communicates with a remote console to remind the patient to take the dosages, and uses a system of coloured lights to indicate that a dose should be taken. The disclosed embodiments are complex to use and understand, may require discarding or adapting existing prescribed preferred or prescribed insulin delivery systems, as well as being prohibitively expensive for many users.

The applicant believes that the abovementioned drawbacks at least partially account for the fact that the majority of insulin pens currently used are not used in conjunction with any means that would help a user determine whether a given dose has been administered.

OBJECT OF THE INVENTION

It is an object of this invention to provide a replaceable cap for a transdermal liquid dosing device which will at least partially alleviate some of the abovementioned problems and which will be relatively cost-effective to manufacture and simple to use.

SUMMARY OF THE INVENTION

In accordance with the invention there is provided a replaceable cap for a transdermal liquid dosing device comprising an elongate hollow body with a first open end which can be placed over a front part of the dosing device from which the liquid is dosed and a second closed end opposite the first end, the cap being releasably received on the dosing device, characterized in that the cap body includes a cavity which opens into the interior of the cap body and which houses a timer unit coupled to a switch mechanism which stands at least partially proud of the cavity so as to project into the interior of the body, and a timer display unit which displays time counted by the timer unit on an outer surface of the body of the cap, wherein the switch mechanism is engaged by abutment of a surface of the front part of the dosing device when the cap is placed on the dosing device, and the switch mechanism is released when the cap is removed from the dosing device, the engagement and/or releasing of the switch mechanism causing the timer unit to reset either immediately or after a predetermined period of time, the time since the timer unit was last reset thereby indicating the time that has elapsed since the dosing device was last used.

Still further features of the invention provide for the body of the cap to include two main parts that connect together to form the cap, with the cavity being defined at least partly between the two main parts so that the two main parts hold the timer unit and switch mechanism captive between them; for the two main parts to be a cap top and a cap bottom that are made from plastic injection moulded material; for the cap top to have a window through which the timer display unit is visible; and for the cap bottom to comprise most of the length of the elongate hollow body.

Yet further features of the invention provide for the cap top to include a flange with a free end that extends towards the first open end and forms a pocket clip.

Further features of the invention provide for the second closed end of the cap to have a battery compartment provided therein; for the battery compartment to be formed in the cap top; and for the battery compartment to have a cover which fits into place to hold the battery securely therein. The cover may be colour-coded to enable a user thereof to match the cap with a particular dosing device in order to distinguish between different dosing devices.

Still further features of the invention provide for the replaceable cap to include a removable non-conductive film initially provided between the battery and an associated electrical battery contact, the film extending through a slot in the cap top to form a projecting tongue that can, prior to use of the cap, be gripped by a user to pull the film out of the battery compartment to enable the battery to engage the contact, the film thereby preventing the battery from being expended prior to use of the cap. The slot may be provided adjacent the window in the cap top and the film initially provided to extend across the timer display unit so that the film also acts as a protective layer for the timer display unit. The portion of the film which covers the timer display unit may also have printed digits thereon to mimic the display of the LCD, so that a user has an indication of what the display will look like once the battery powers the LCD.

Yet further features of the invention provide for the timer unit to include electronic circuitry on a printed circuit board (PCB); and for the timer unit, timer display unit and switch mechanism to be mounted together as a single control unit which fits in the cavity.

Further features of the invention provide for the timer display unit to be a low-cost four digit digital liquid crystal display (LCD); for the timer unit to count up from zero; for the timer to be reset to zero by the releasing of the switch mechanism, and for the timer unit to be configured to, during the first 59 minutes and 59 seconds of elapsed time, use the first two digits for counting minutes and the last two digits for counting seconds, and thereafter, to use the first two digits for counting hours and the second two digits for counting minutes.

Still further features of the invention provide for the cavity to be of a standard size so that the same control unit can fit into multiple different caps where each cap has inner surface dimensions sized to fit a specific type of dosing device, the control unit thereby being capable of being mass produced for all caps with an attendant increase in the economies of scale.

Yet further features of the invention provide for the switch mechanism to include a leaf spring that projects into the interior of the body; for the leaf spring to be oriented so that it is has a fixed end closer to the first, open end of the body and a free end closer to the second, closed end of the body so that the act of inserting the front part of the device into the cap causes the leaf spring to flex towards the cavity without the free end hooking on any features at the front part of the device; and for the leaf spring to be mounted so as abut an electromechanical switch so as to actuate the switch when the leaf spring is bent towards the cavity. The leaf spring may be made from spring steel and may have sufficient flex no that differently shaped front parts of different devices will all engage the leaf spring sufficiently so as to activate the switch.

Further features of the invention provide for the timer unit to reset only after the elapse of the predetermined period of time; and for the predetermined period of time to be between 5 and 12 seconds; to thereby prevent the timer unit from being reset in the event that a user only briefly removes the cap as may occur when a user inspects liquid level in the dosing device or when a user inadvertently removes the cap for a short period of time.

Still further features of the invention provide for the inner dimensions of the replaceable cap body to be chosen to match the inner dimensions of an existing cap which is initially provided together with the device, the replaceable cap thereby providing the same or very similar push or snap fit onto the dosing device as the existing cap.

Yet further features of the invention provide for the dosing device to be disposable and the replaceable cap to also be disposable but to be capable of being used successively in relation to at least several disposable dosing devices.

Further features of the invention provide for the timer display unit 10 include a battery level indicator or warning which provides an indication as to when the battery is low. The cap may be disposable after the battery has been depleted, or the battery compartment cover may be removable to permit the battery to be replaced by a user.

Still further features of the invention provide for the dosing device to be an insulin pen that includes a reservoir and a hypodermic needle provided at the front part of the device.

The invention extends to a replaceable cap for a transdermal liquid dosing device comprising an elongate hollow body with a first open end which can be placed over a front part of the dosing device from which the liquid is dosed and a second closed end opposite the first end, characterized in that the body has two main injection moulded plastic parts that connect together to form the body of the cap, the two parts holding a control unit captive between them in a cavity defined between the two parts, wherein the control unit includes a timer unit, a timer display unit which displays time counted by the timer unit on an outer surface of the body, and a switch mechanism, the switch mechanism being configured to be actuated when the cap is placed on the dosing device and/or when the cap is removed from the dosing device, the actuation of the switch mechanism causing the timer unit to reset either immediately or after a predetermined period of time, the time since the timer unit was last reset thereby indicating the time that has elapsed since the dosing device was last used.

BRIEF DESCRIPTION OF THE DRAWINGS

The invention will now be described, by way of example only with reference to the accompanying representations in which:

FIG. 5 is a state diagram showing the various states that a control unit of the cap can be in.

DETAILED DESCRIPTION WITH REFERENCE TO THE DRAWINGS

Figure 1A:
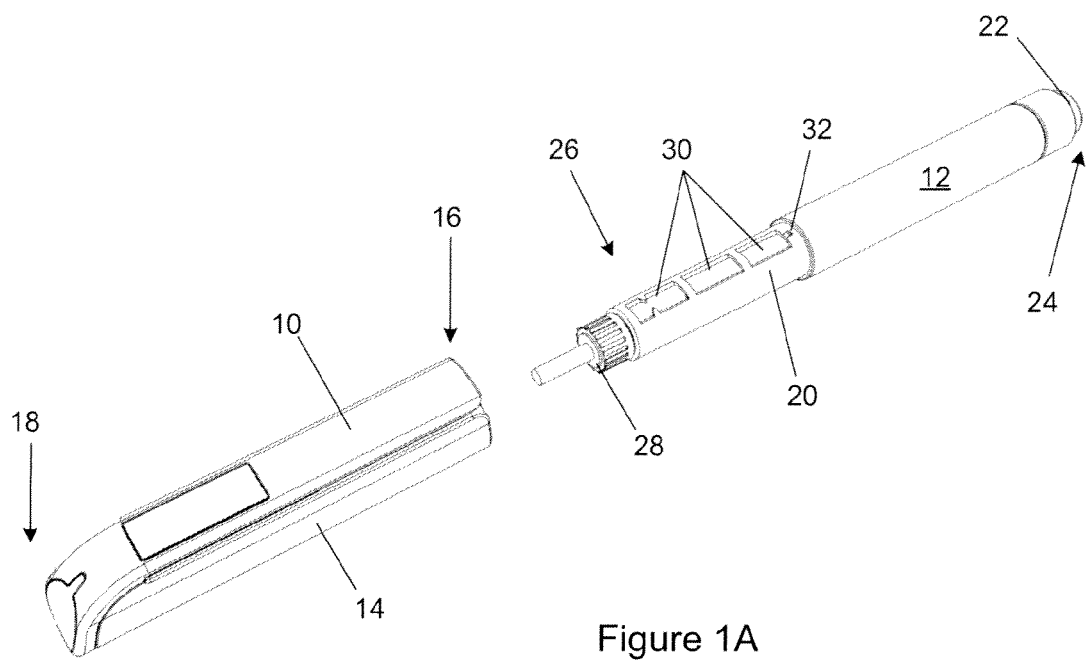
FIG. 1A is a perspective view of a replaceable cap according to the invention and a dosing device, with the cap separated from the dosing device.

FIG. 1A shows a perspective view of a replaceable cap (10) according to the invention and an associated dosing device (12). The cap comprises an elongate hollow body (14) with a first open end (16) and a second closed end (18) opposite the first end. In this embodiment, the dosing device is a disposable insulin pen that includes a reservoir (20) in which liquid insulin is held, a plunger (22) at a back end (24) of the insulin pen, and a hypodermic needle (not shown) from which the insulin is dosed at the tip of a front part (26) of the insulin pen. The hypodermic needle has a removable sheath (28) for covering the needle. Along the body of the insulin pen and adjacent the front part, a transparent section or sections (30) are provided by means of which the level of liquid insulin can be checked by visual inspection. The insulin pen may be a pre-existing disposable insulin pen as commonly available in the market, which is supplied with an existing cap which can simply be discarded and replaced by the replaceable cap of the invention.

Figure 1B:
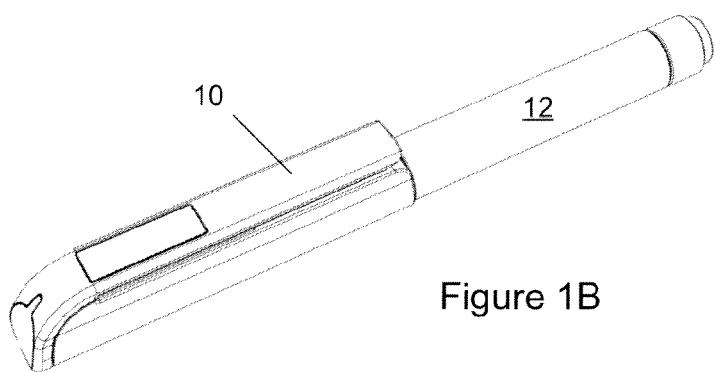
FIG. 1B is similar to FIG. 1A but shows the replaceable cap on the dosing device.

The first open end (16) of the cap can be placed over the front part (26) of the dosing device so that the cap fits onto the dosing device and covers the front part, as shown in FIG. 1B where the cap is shown on the dosing device. The cap is releasably retained on the dosing device and has inner dimensions (not shown) sized to fit a specific type of dosing device, the inner dimensions being chosen to match the inner dimensions of the existing cap initially provided with the dosing device, so that the cap of the invention provides the same or very similar push or snap fit onto the dosing device as the existing cap.

Figure 2:
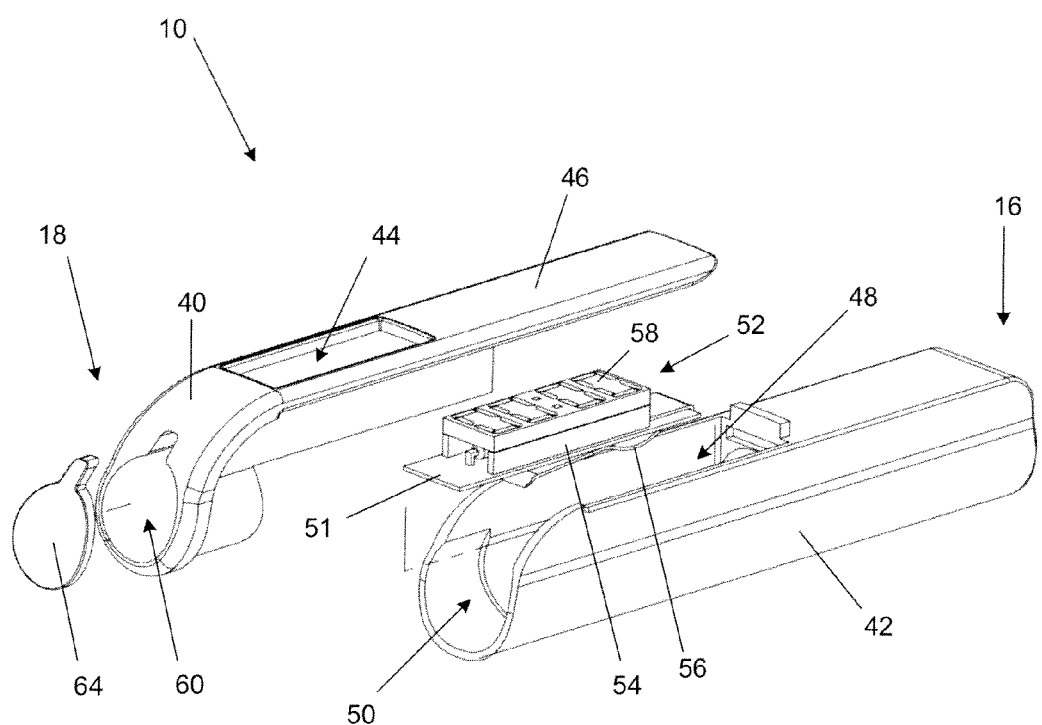
FIG. 2 is an exploded view of the components of the replaceable cap of FIG. 1.

FIG. 2 shows an exploded view of the components of the replaceable cap (10). The replaceable cap includes two main parts, a cap top (40) and a cap bottom (42) that connect together to form the cap. The cap top and cap bottom are plastic injection moulded components and may be connected together by clips, ultrasonic welding, glue or any other suitable means. The cap bottom forms most of the length of the elongate cap body, and the cap top has a rectangular shaped window (44) provided therein. A flange (46) extends along an upper side of the cap top (4)) towards the first open end (16) to form a pocket clip.

When assembled, a cavity (48) is formed between the cap top and the cap bottom. The cavity opens into the interior (50) of the cap body and aligns with the window (44). The cavity houses a control unit (52) which fits snugly into the cavity and is held captive by the cap top and cap bottom, and comprises a printed circuit board (PCB) (51) on which a timer unit (54), a switch mechanism (56), and a timer display unit (58) are mounted. The PCB can be a single layer PCB in some embodiments and may be as thin as 0.5 mm. In this embodiment the timer display unit (58) is a low-cost four digit digital liquid crystal display (LCD) which displays the time counted by the timer unit, and the timer display unit aligns with the window (44) so that it is visible at the upper surface of the cap top. The timer display may include a low battery warning indicator, and is preferably not back-lighted to save power. The timer unit consists of a microcontroller counter and an oscillating crystal, and is preferably a 4 bit, low voltage (e.g. 0.9-1.7 V) masked ROM microcontroller with a built-in LCD driver. A digital watch integrated circuit could also be used for this purpose.

At the second closed end (18) of the cap, a battery compartment (60) is formed in the cap top. The battery compartment is provided at the second end so as to be as far as possible from the liquid insulin reservoir of the dosing device, and is fowled as a separate compartment so as to minimize the risk that any battery leakage could contaminate the insulin stored in the insulin reservoir of the insulin pen. The battery may be a silver oxide non-rechargeable 1.5 V battery that has sufficient stored charge to power the control unit for a period of at least several months, such as even more than 12 months and up to 36 months, the cap thereby being capable of being used successively in relation to many disposable insulin pens.

Figure 3:
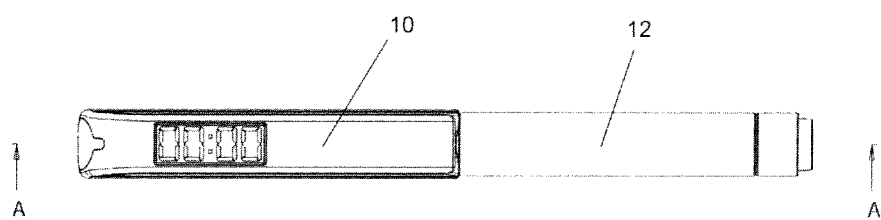
FIG. 3 is a top plan view of the replaceable cap on the dosing device.
Figure 4:
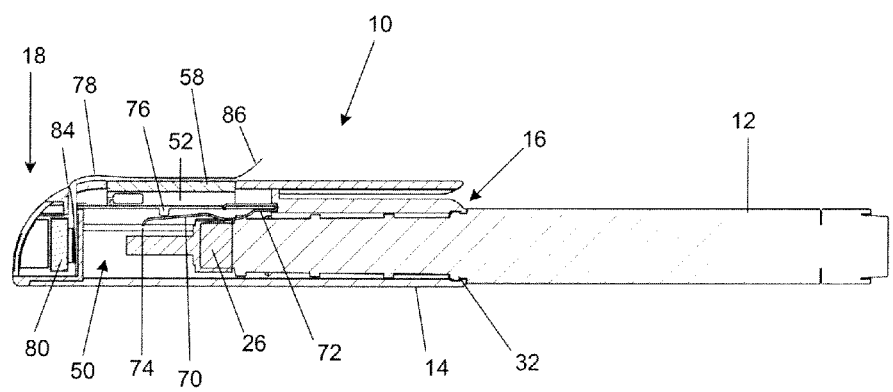
FIG. 4 is a sectional elevation along line A-A in FIG. 3.

The battery is held in place against a set of electrical contacts (not shown) by means of a cover (64) which fits into place. The cover is preferably colour-coded to enable the user to distinguish between multiple insulin pens which may be in use at any given time. In some embodiments, the cap is disposable and is intended to be discarded once the battery is depleted, in which case the cover may be permanently affixed in place by means of gluing, ultrasonic welding or deforming clipping formations. In other embodiments, the cover may be opened by prising or unscrewing it so as to replace the battery. FIG. 3 shows a top plan view of the replaceable cap (10) and the dosing device (12) with the cap on the dosing device, and FIG. 4 shows a sectional elevation along line A-A of FIG. 3. As shown in FIG. 4, the switch mechanism includes a leaf spring (70) that stands partially proud of the cavity in which the control unit (52) is mounted, and projects into the interior (50) of the cap body. The leaf spring is oriented so that it has a fixed end (72) closer to the first, open end (16) of the cap body and a free end (74) closer to the second, closed end (18) of the body. The leaf spring is mounted so as to abut an electromechanical switch (76) on the PCB so as to actuate the switch when the leaf spring is bent towards the cavity. The act of inserting the front part (26) of the insulin pen (12) into the open end of the cap causes the surface of the front part to abut the leaf spring and cause it to flex towards the cavity and depress the switch (76). Because the leaf spring is oriented with its free end closer to the closed end of the body, the free end does not hook onto any features, such as ridges or shoulders, that may be present on the front part (26) of the dosing device as might happen if the leaf spring was oriented in the opposite direction. The leaf spring is preferably made from spring steel and has sufficient flex so that differently shaped front parts of different insulin pens will all engage the leaf spring sufficiently to activate the switch.

Importantly, the cavity (50) in which the control unit (52) fits is chosen to be of a standard size so that the same control unit can fit into multiple different caps according to the invention, where each cap has inner surface dimensions sized to fit a specific type of dosing device. Preferably, the inner surface dimensions of each type of cap are chosen to match the inner surface dimensions of the existing cap which is initially provided together with that type of insulin pen, the replaceable cap of the invention thereby providing the same or very similar snap fit as the existing cap provided with the pen. Having the cavity of a standard size makes it possible for the same control unit to fit into every different kind of cap, the control unit thereby being capable of mass production with the attendant increase in the economies of scale. It is also important in this regard that, as previously mentioned, the leaf spring has sufficient flex so that differently shaped front parts of different insulin pens will all engage the leaf spring sufficiently to activate the switch. The same switch mechanism can therefore be used on all control units.

As also seen in FIG. 4, a removable non-conductive film (78) is provided between the battery (80) and one of its associated electrical contacts (not shown). The non-conductive film extends through a slot (84) which is provided adjacent the window in the cap top and extends across the timer display unit (58) and ends in a projecting tongue (86). The removable non-conductive film will be put in place during manufacture and is intended to remain in place until actual use of the cap by a patient. When a patient is ready to use the cap, the tongue is gripped between the thumb and forefingers and the film is pulled off the timer display and out of the battery compartment, causing the battery to engage the electrical contacts. The film thereby prevents the battery from being expended prior to use, greatly increasing the shelf life of the replaceable cap of the invention. The portion of the film which covers the timer display unit may also have printed digits thereon to mimic the display of the LCD, so that a user has an indication of what the display will look like once the battery powers the LCD.

In use, the electromechanical switch (76) is actuated when the cap is fully inserted onto the insulin pen, and the switch is released when the cap is removed from the insulin pen. Either the engaging or the releasing of the switch causes the timer unit to reset the timer after the elapse of a predetermined period of time, which is preferably between 5 and 12 seconds, most preferably about 8 seconds. Upon resetting the timer, the timer display unit resets the LCD to zero, after which the timer unit starts displaying the time that has elapsed since the timer was last reset. In this way, the replaceable cap of the invention indicates to a patient the time that has elapsed since the insulin pen was last used.

The reason that the timer is preferably not reset immediately upon engaging or releasing of the switch is that users of insulin pens sometimes briefly remove the insulin pen cap to merely check the levels of liquid insulin by means of the transparent sections (30), without also performing an insulin injection. This action typically takes only 2 or 3 seconds, whereas the action of injecting insulin typically takes at least 12 seconds. Also, a user may inadvertently remove or partially remove the cap for a short period, such as occurs when fiddling with pens or other devices. An assumption is therefore made that if the cap has been off for longer than the predetermined time, then a user has taken a prescribed dose of insulin and the timer is reset. In this way, by simply looking at the digital timer display unit, a patient can confirm the time that has elapsed since a last dosage has taken place, thereby avoiding the anxiety of wondering if the previous dose has been forgotten or the previous dose has just been taken, and diminishing the risk of accidental over- or under-dosing taking place.

In the preferred embodiment the four digit LCD counts upwards from zero and uses the first two digits for counting minutes and the last two digits for counting seconds during the first 59 minutes and 59 seconds following the last time that the timer was reset. When the timer reaches 60 minutes, the first two digits are then used for counting hours and the second two digits used for counting minutes. In this way, it is possible to use only a four digit LCD rather than a more expensive six digit LCD, while still being able to indicate seconds to a user during the first hour following the last insulin dosage.

Figure 5:
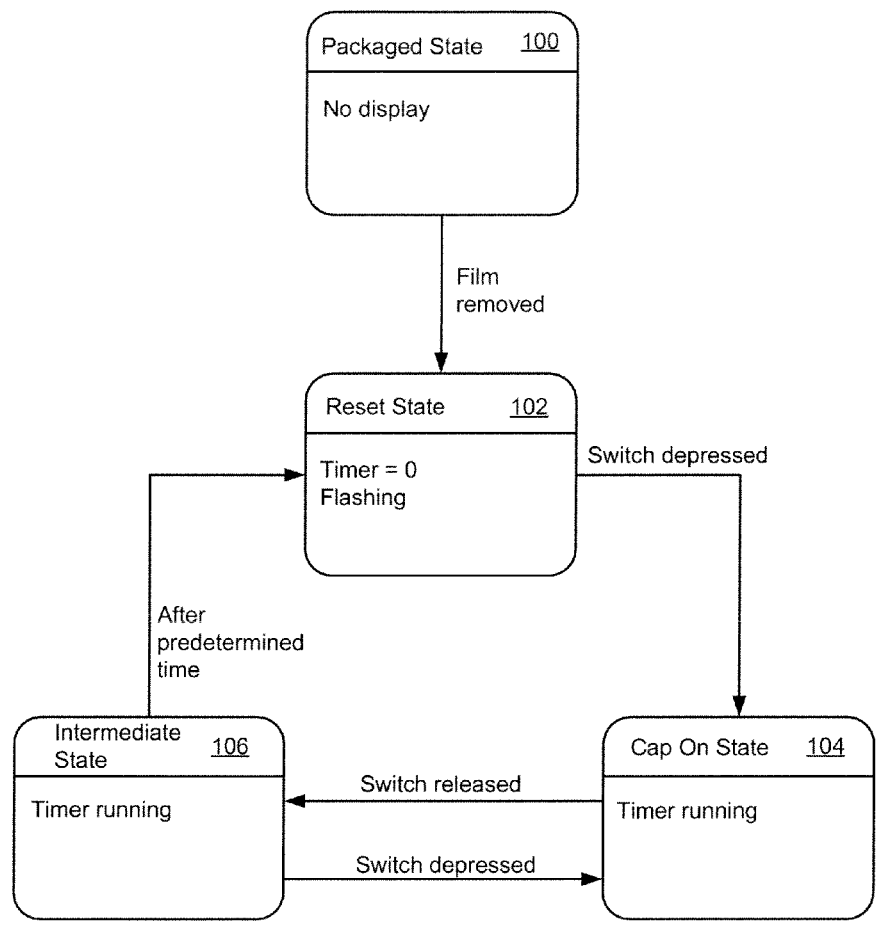

FIG. 5 is a state diagram showing the states that the control unit can be in. When packaged, the control unit is in a packaged state (100) during which nothing is displayed on the LCD because the battery is disconnected. Once the film is removed, the control unit enters a reset state (102) during which the timer is reset and held at zero, and all segments of the LCD flash. Depressing the switch, as happens when the cap is placed on the insulin pen for the first time, causes the control unit to enter a "cap on" state (104) during which the timer runs and the running time is displayed on the LCD. During the "cap on" state, the four digit timer will use the first two digits for minutes and the last two digits for seconds during the first 59 minutes and 59 seconds of elapsed time, and thereafter use the first two digits for hours and the last two digits for minutes, as previously explained. The timer may be configured to count up to 99 hours and 59 minutes. If the switch is released following the "cap on" state, as occurs when the cap is removed, then the control unit enters an intermediate state (106).

During the intermediate state, the timer continues to run for a predetermined period which may, for example, be 8 seconds. If the switch is depressed again before the end of the predetermined period (e.g. if the cap is replaced quickly after removing it) then the control unit re-enters the "cap on" state (104). If, however, the cap is not replaced within the predetermined period, then the control unit enters the reset state (102) and the timer is reset and held at zero with all segments of the LCD flashing as previously described.

The invention provides a simple-to-use and cost effective replaceable cap for a dosage device by means of which a patient can confirm the time that has elapsed since a last dosage has taken place. The invention does not require a user to carry any additional equipment as the cap simply replaces the existing cap that is supplied with the dosing device. No special instructions need to be followed, no timing schemes using flashing lights or other non-numerical indicators need to be learned and memorized, and no change in the procedure of using the dosage device needs to be made by the patient. The cap can easily be used by anyone familiar with a digital clock, which should include the very young and the very frail. In addition, because the inner dimensions of the replaceable cap are selected to match the inner dimensions of the original cap which is replaced, the cap of the invention has the same snap-fit or push-fit feel as the original cap, and the switching mechanism does not interfere in any way with how securely the cap fits onto the dosing device. The cap top and cap bottom can made by basic two part injection moulding, and since no moving parts are required to be moulded into the cap the cap can therefore be moulded very cost-effectively. Because the cavity in which the control unit is fitted is standard across all different types of caps, the control units can be mass produced which leads to a further reduction in the cost of the caps.

While the invention has described with reference to a specific embodiments, it will be appreciated that the invention is not limited to the described embodiment, and that variations may be made without departing from the scope of the invention. For example, the switch mechanism need not include a leaf spring but could include a dome switch or a conductive elastomeric switch. In other embodiments, a capacitive sensor can detect the presence of the front part of the insulin pen without requiring physical contact or a moving part, which would facilitate sealing of the electronic components. An optical sensor could also be used by either reflecting a beam off an internal surface of the cap which would be interrupted by the insulin pen, or by sensing ambient light. The replaceable cap of the invention could be used with other kinds of dosing devices, such as epinephrine auto-injectors, anti-retroviral pens or other dosing devices which make use of a replaceable cap. The timer unit need not count up, but could count down, thereby indicating the time remaining until the next dosage is due.

Having thus described the invention, it is now claimed:

1. A replaceable cap for a transdermal liquid dosing device comprising an elongate hollow generally tubular body with a first open end which can be placed over a front part of the dosing device from which the liquid is dosed and a second closed end opposite the first end, the cap being releasably received on the dosing device, wherein the cap body includes a cavity which houses a timer unit coupled to a switch, and a timer display unit which displays time counted by the timer unit on an outer surface of the body of the cap, wherein the switch is opened or closed by the presence of a surface of the front part of the dosing device when the cap is placed on the dosing device, and the switch is closed or opened when the cap is removed from the dosing device, the operation of the switch causing the timer unit to reset either immediately or after a predetermined period of time, the time since the timer unit was last reset thereby indicating the time that has elapsed since the dosing device was last used, and wherein the elongate hollow body of the cap includes two main parts that are of injection moulded plastic and that connect together to form the cap with the cavity being defined at least partly between the two main parts, and wherein the two main parts hold the timer unit and switch captive between them.

2. A replaceable cap as claimed in claim 1 in which the switch is in the form of an electromechanical switch that projects into the interior of the cap body to cooperate with an outer surface of the liquid dosing device.

3. A replaceable cap as claimed in claim 1 in which the two main parts are a cap top that has a window through which the timer display unit is visible and a flange with a free end that extends towards the first open end to form a pocket clip, and a cap bottom that forms most of the length of the elongate hollow body.

4. A replaceable cap as claimed in claim 1 in which the second closed end has a battery compartment provided therein, the battery compartment having a cover which fits into place to hold a battery securely therein.

5. A replaceable cap as claimed in claim 4 in which the cover is colour-coded to enable a user thereof to match the cap with a particular dosing device in order to distinguish between different dosing devices.

6. A replaceable cap as claimed in claim 4 in which a removable non-conductive film is initially provided between the battery and an associated electrical battery contact, the film extending through a slot in the cap body and across an outer surface of the timer display unit to terminate in a projecting tongue that can, prior to use of the cap, be gripped by a user to pull the film out of the battery compartment to enable the battery to engage the battery contact.

7. A replaceable cap as claimed claim 1 in which the timer display unit is a mass produced four digit digital liquid crystal display (LCD), the timer unit is configured to count up from zero, the timer is reset to zero by the releasing of the switch, and the timer unit is configured to, during the first 59 minutes and 59 seconds of elapsed time since the dosing device was last used, use the first two digits for counting minutes and the last two digits for counting seconds, and thereafter, to use the first two digits for counting hours and the second two digits for counting minutes.

8. A replaceable cap as claimed in claim 1 in which the timer unit includes electronic circuitry on a printed circuit board (PCB), and the timer unit, timer display unit and switch mechanism are mounted together as a single control unit in the cavity.

9. A replaceable cap as claimed in claim 8 in which the cavity is of a standard size so that the same control unit can fit into multiple different caps where each cap has inner surface dimensions sized to fit a specific type of dosing device, the control unit thereby being capable of being mass produced for all caps.

10. A replaceable cap as claimed in claim 2 in which the switch mechanism includes a leaf spring that projects into the interior of the cap body and is mounted so as to abut the electromechanical switch, so that the leaf spring actuates the electromechanical switch when the leaf spring is bent towards the cavity.

11. A replaceable cap as claimed in claim 10 in which the leaf spring is oriented so that it is has a fixed end closer to the first, open end of the body and has free end closer to the second, closed end of the body, so that the act of inserting the front part of the device into the cap causes the leaf spring to flex towards the cavity without the free end hooking on any features at the front part of the device.

12. A replaceable cap as claimed in claim 10 in which the leaf spring is made from spring steel and has sufficient flex so that differently shaped front parts of different devices will all engage the leaf spring sufficiently so as to actuate the switch.

13. A replaceable cap as claimed in claim 1 in which the timer unit resets after the elapse of the predetermined period of time, and the predetermined period of time is between 5 and 12 seconds, to thereby prevent the timer unit from being reset in the event that a user only briefly removes the cap.

14. A replaceable cap as claimed in claim 1 in which inner dimensions of the replaceable cap body are chosen to match inner dimensions of an existing cap which is initially provided together with the dosing device, the replaceable cap thereby providing the same or very similar push or snap fit onto the dosing device as the existing cap.

15. A replaceable cap as claimed in claim 1 in which the dosing device is a disposable insulin pen that includes a reservoir and a hypodermic needle provided at the front part of the dosing device, and the replaceable cap is also disposable but is capable of being used successively in relation to at least several disposable insulin pens.

* * * * *